(12) United States Patent
Philippo et al.

(10) Patent No.: US 6,331,549 B1
(45) Date of Patent: Dec. 18, 2001

(54) 1-AMINOETHYLQUINOLINE DERIVATIVES FOR TREATING URINARY INCONTINENCE

(75) Inventors: Christophe Philippo; Patrick Mougenot, both of Rueil-Malmaison; Gérard Defosse, Paris; Alain Braun, Boulogne Billancourt; Philippe Bovy, Mareil Marly, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/831,442

(22) PCT Filed: Nov. 10, 1999

(86) PCT No.: PCT/FR99/02760

§ 371 Date: May 9, 2001

§ 102(e) Date: May 9, 2001

(87) PCT Pub. No.: WO00/29379

PCT Pub. Date: May 25, 2000

(30) Foreign Application Priority Data

Nov. 17, 1998 (FR) .................................................. 98/14398

(51) Int. Cl.$^7$ .......................... C07D 215/14; A61K 31/47
(52) U.S. Cl. .............................................. 514/311; 546/176
(58) Field of Search .............................. 514/311; 546/176

(56) References Cited

FOREIGN PATENT DOCUMENTS

| 2752840 | 3/1998 | (FR) . |
|---|---|---|
| WO 97/32870 | 9/1997 | (WO) . |
| WO 98/08834 | 3/1998 | (WO) . |

OTHER PUBLICATIONS

Derwent Patent Abstract No. 230249 (1998).
Derwent Patent Abstract No. 457482 (1997).
Derwent Patent Abstract No. 1817401(1998).

*Primary Examiner*—Zinna Northington Davis
(74) *Attorney, Agent, or Firm*—Michael D. Alexander

(57) ABSTRACT

The invention relates to 1-aminoethylquinoline derivatives, to pharmaceutical compositions containing them, to therapeutic methods of using them and to processes for preparing them.

18 Claims, No Drawings

1-AMINOETHYLQUINOLINE DERIVATIVES FOR TREATING URINARY INCONTINENCE

This is a 371 of PCT/FR99/02760 filed Nov. 10, 1999.

The present invention relates to 1-amino-ethylquinoline derivatives, to their preparation and to their therapeutic application.

The publication Chemical Abstracts, Vol.83, No.9 (Jan. 9, 1975) discloses 8-(1-aminoethyl)quinoline, but describes only the process for preparing it.

According to one of the aspects of the invention, it relates to compounds corresponding to the general formula (I)

(I)

in which:

A represents a hydrogen atom, an azido, a halogen, a hydroxyl, a thiol, an amino, a phenyl, a $C_{1-6}$ alkyl, $C_{1-6}$ alkylamino, di($C_{1-6}$ alkyl)amino, hydroxylamine, $C_{1-6}$ alkylhydroxylamine, $N,O-C_{1-6}$ dialkylhydroxylamine, $C_{1-6}$ alkoxy or $C_{1-6}$ alkylsulphanyl group, B and D represent, independently of each other, a hydrogen atom, a phenyl, a $C_{1-6}$ alkyl, $C_{2-6}$ alkenyl, $C_{1-6}$ fluoroalkyl or $C_{1-2}$ perfluoroalkyl group, or together form an oxo, $R_1$ represents a hydrogen atom, a halogen, a carbonyl, a hydroxycarbonyl, a cyano, a carboxamide, a $C_{1-6}$ alkyl, $C_{2-6}$ alkenyl, $C_{3-6}$ cycloalkyl, $C_{1-6}$ alkoxycarbonyl, $C_{1-6}$ hydroxyalkyl, $C_{1-6}$ alkoxy, $(C_{1-6})$alkoxy$(C_{1-3})$ alkyl, $C_{1-6}$ fluoroalkyl, $C_{1-2}$ perfluoroalkyl or $CF_3(OH)$ CH group, or $R_1$ and $R_2$ together form a $C_{3-5}$ alkylene or $C_{3-5}$ alkenylene chain or form, with the carbon atoms to which they are attached, a phenyl, $R_2$, $R_3$ and R4 represent, independently of each other, a hydrogen atom, a halogen or a $C_{1-6}$ alkyl group, or $R_2$ and $R_3$ together form a $C_{3-5}$ alkylene or $C_{3-5}$ alkenylene chain or $R_1$ and $R_2$, together, are as defined above, and $R_5$ and $R_6$ represent, independently of each other, a hydrogen atom, a $C_{1-6}$ alkyl, $C_{2-6}$ alkenyl, $C_{3-6}$ cycloalkyl, $C_{3-6}$ cycloalkenyl, $C_{1-6}$ fluoroalkyl or $C_{1-2}$ perfluoroalkyl group or $R_5$ and $R_6$ together form a $C_{2-6}$ alkylene or $C_{3-6}$ alkenylene chain, to give, with the nitrogen to which they are attached, a heterocycle such as, for example, a piperidyl, azetidinyl or pyrrolidyl, this heterocycle optionally being substituted with a $C_{1-4}$ alkyl group, and salts thereof.

The compounds that are preferred according to the invention are chosen from the following subgroups, in which:

A represents a halogen, a hydroxyl, a thiol, a phenyl or a $C_{1-6}$ alkyl, hydroxylamine, $C_{1-6}$ alkylhydroxylamine, $N,O-C_{1-6}$ dialkylhydroxylamine, $C_{1-6}$ alkoxy or $C_{1-6}$ alkylsulphanyl group, and more particularly a hydroxyl, a phenyl or a $C_{1-6}$ alkyl, $N,O-C_{1-6}$ dialkylhydroxylamine or $C_{1-6}$ alkoxy group; or B and D represent, independently of each other, a hydrogen atom, a phenyl or a $C_{1-6}$ alkyl group or together form an oxo; or $R_1$ represents a $C_{1-6}$ alkyl, $C_{2-6}$ alkenyl, $C_{1-6}$ fluoroalkyl or $C_{1-2}$ perfluoroalkyl, more particularly $C_{1-6}$ alkyl or $C_{1-2}$ perfluoroalkyl or $CF_3(OH)CH$ group, or $R_1$ and $R_2$ together form a $C_{3-5}$ alkylene or $C_{3-5}$ alkenylene chain, more particularly a $C_{3-5}$ alkylene chain, or $R_1$ and $R_2$ form, with the carbons to which they are attached, a phenyl; or $R_5$ and $R_6$ represent, independently of each other, a $C_{1-6}$ alkyl or $C_{2-6}$ alkenyl group, or $R_5$ and $R_6$ together form a $C_{2-6}$ alkylene or $C_{3-6}$ alkenylene chain, to give, with the nitrogen to which they are attached, a heterocycle, this heterocycle optionally being substituted with a $C_{1-4}$ alkyl and more particularly $C_{1-2}$ alkyl group.

One subgroup of compounds of formula (I) which is particularly preferred is the one in which A, B, D, $R_1$, $R_5$ and $R_6$ are as defined above in the subgroups of preferred compounds, and $R_2$, $R_3$ and R4 are as defined above.

In particular, the subgroup of compounds below is particularly preferred:

A represents a hydroxyl, a phenyl or a $C_{1-3}$ alkyl, $N,O-C_{1-3}$ dialkylhydroxylamine or $C_{1-3}$ alkoxy group;

B and D represent, independently of each other, a hydrogen atom, a phenyl or a $C_{1-3}$ alkyl group or together form an oxo;

$R_1$ represents a $C_{1-3}$ alkyl or $C_{1-2}$ perfluoroalkyl group or $R_1$ and $R_2$ together form a $C_{3-5}$ alkylene chain, or $R_1$ and $R_2$ form, with the carbons to which they are attached, a phenyl;

$R_2$, $R_3$ and $R_4$ represent, independently of each other, a hydrogen atom, a halogen or a $C_{1-3}$ alkyl group, or $R_2$ and $R_3$ together form a $C_3$–$C_5$ alkylene chain, or $R_1$ and $R_2$, together, are as defined above, $R_5$ and $R_6$ represent, independently of each other, a $C_{1-6}$ alkyl group, or $R_5$ and $R_6$ together form a piperidyl, this piperidyl optionally being substituted with a $C_{1-2}$ alkyl group.

In the present patent application:

$C_{1-z}$ (or $C_{2-z}$ or $C_{3-z}$), in which z may take values between 2 and 6, represents a carbon-based chain which may contain from 1 (or 2 or 3) to z carbon atoms, the terms alkyl, alkenyl and alkoxy represent, respectively, an alkyl, alkenyl or alkoxy containing a linear or branched carbon-based chain, the terms alkylene and alkenylene represent, respectively, a divalent alkyl or alkenyl containing a linear or branched carbon-based chain, Pg represents a protecting group; examples of protecting groups and methods of protection and deprotection are given in Protective groups in *Organic Synthesis Greene* et al., 2nd Ed. (John Wiley & Sons, Inc., New York), and halogen represents an iodine, bromine, chlorine or fluorine atom.

The compounds of general formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

When a compound according to the invention shows stereoisomerism, for example of axia-equatorial or Z-E type, the invention comprises all the stereoisomers of these compounds.

The compounds of general formula (I) may be in the form of the free base or in the form of addition salts with acids, which also form part of the invention. According to the present invention, these salts comprise those with mineral or organic acids which allow a suitable separation or crystallization of the compounds of formula (I), such as picric acid, oxalic acid or an optically active acid, for example a tartaric acid, a dibenzoyltartaric acid, a mandelic acid or a camphorsulphonic acid, and those which form physiologically acceptable salts, such as the hydrochloride, hydrobromide, sulphate, hydrogen sulphate, dihydrogen phosphate, maleate, fumarate, 2-naphthalenesulphonate, pamoate or para-toluene-sulphonate.

Although the pharmaceutically acceptable salts are preferred, the other salts form part of the present invention. These salts may be prepared according to methods known to those skilled in the art, for example by reacting the base with the acid in a suitable solvent, such as an alcoholic solution or an organic solvent, followed by separation from the medium containing it by evaporating off the solvent or by filtration.

The compounds of the invention may be prepared according to processes illustrated by the schemes which follow. The preparation processes form part of the present invention.

1. The compounds of formula (I), in particular those for which A represents a hydroxyl group, may be prepared according to the process described in Scheme 1.

formula II. The hydroxyl group borne by the carbon alpha to the heterocycle in the compound thus obtained is activated, in a manner which is known to those skilled in the art, so as to give a nucleofugal group such as a mesyl or tosyl group or a bromine atom. The compound of formula (I) according to the invention is then prepared from this compound by reacting the latter with an excess of amine $NHR_5R_6$, in an organic solvent such as chloroform, acetonitrile or tetrahydrofuran. The reaction is preferably performed in dichloromethane in the presence of triethylamine. This reaction is followed by a deprotection according to methods known to those skilled in the art, for example, in the case of a silyl ether, the hydroxyl group is deprotected by the action of tert-butylaimonium fluoride. The meanings of $R_1$, $R_2$, $R_3$, $R_4$, $R_5$, $R_6$, B and D in each of the compounds of formulae II, III and IV and of the amine $NHR_5R_6$ are those given for formula (I).

The ethenyl derivative of formula IV may itself be prepared from a quinoline derivative of formula V, in which Y represents a nucleofugal group such as a halogen, or a hydroxyl group activated, for example, as a triflate, by Stille palladium coupling with a compound of formula VI, B and D having the same meanings as for the compounds of formula (I), under the conditions defined by D. R. McKean et al. (J. Org. Chem. 1987; 52: 492).

Alternatively, the ethenyl derivative of formula IV may be prepared from an aldehyde derivative of formula XIV, by a

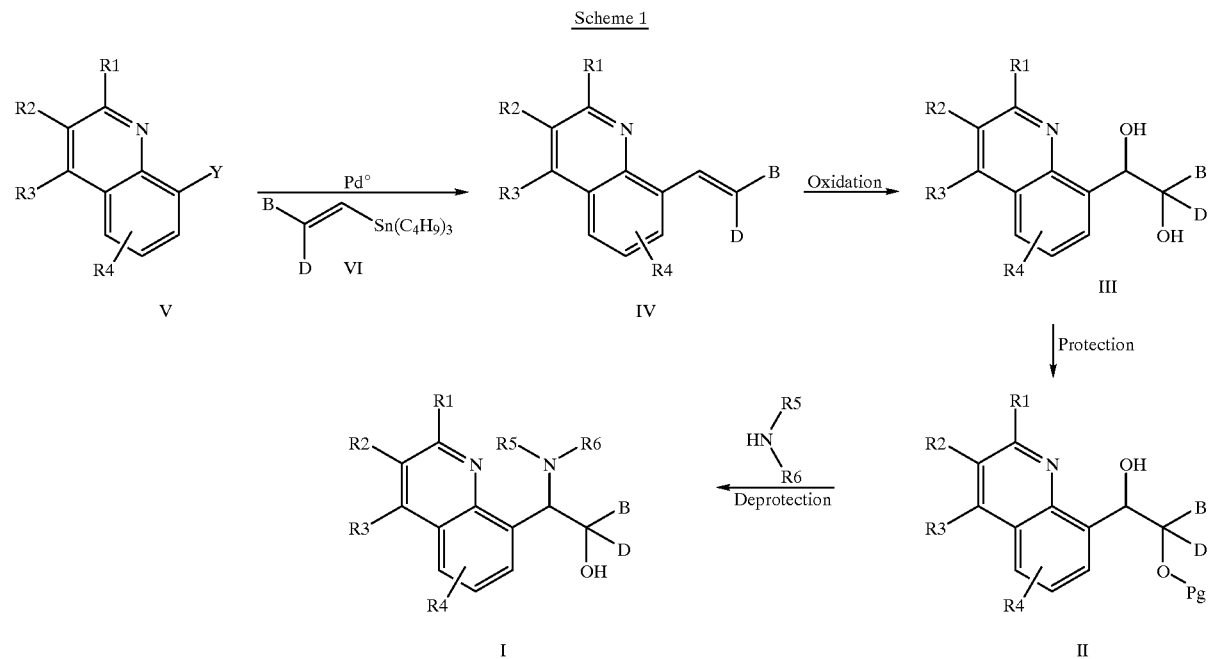

Scheme 1

According to this process, an ethenyl derivative of formula IV is reacted with an oxidizing agent, such as sodium periodate, osmium tetroxide or meta-chloroperbenzoic acid, in basic or acidic medium so as to form a diol of formula III. The hydroxyl group geminal to the group B (or D) is selectively protected with a protecting group Pg, in a manner which is known to those skilled in the art, for example by forming a silyl ether, so as to obtain the compound of Wittig reaction under conditions that are standard for those skilled in the art. The compounds of formula XIV may themselves be prepared by formylation of a halo derivative of formula V, Y representing halogen, in the presence of N,N-dimethyl-formamide and butyllithium. The formylation reaction may be carried out in an organic solvent such as tetrahydrofuran or N,N-dimethylformamide or a mixture of these solvents, according to the reaction scheme (2) below:

Scheme 2

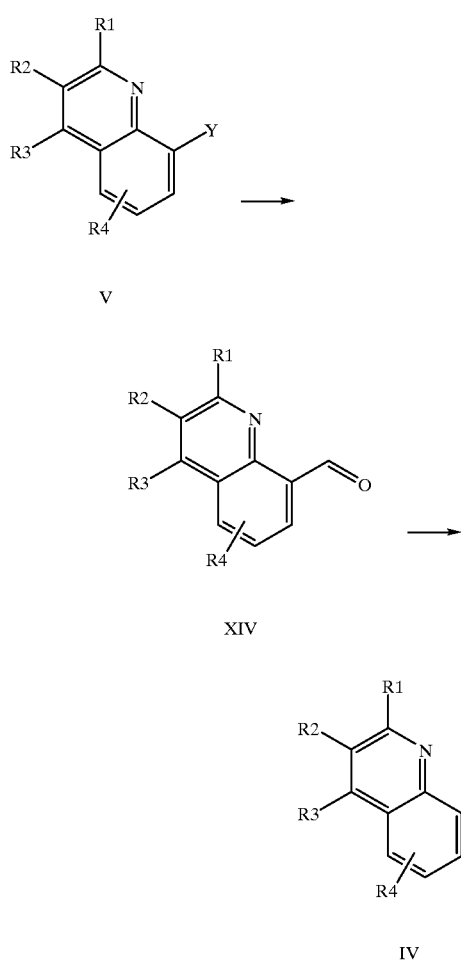

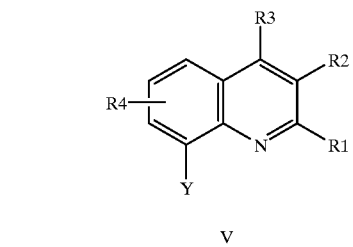

According to this scheme, an aniline of formula VII, for which Y represents a halogen, a hydroxyl or a methoxy, is heated with an α,β-unsaturated aldehyde or ketone of formula VIII in the presence of a dehydrating agent, such as sulphuric acid, and an oxidizing agent, such as sodium iodide, to form a quinoline derivative of formula V which is substituted in position 8 with the group Y. The meanings of $R_1$, $R_2$, $R_3$ and $R_4$ in the compounds of formulae V, VIII and VII are those given in formula I.

Alternatively, the compounds of formula V for which Y represents a hydroxyl group may be prepared by an intramolecular cyclization reaction under the conditions defined by Uchiyama K. et al. (Synlett 1997; 445–446), according to Scheme 4.

Scheme 4

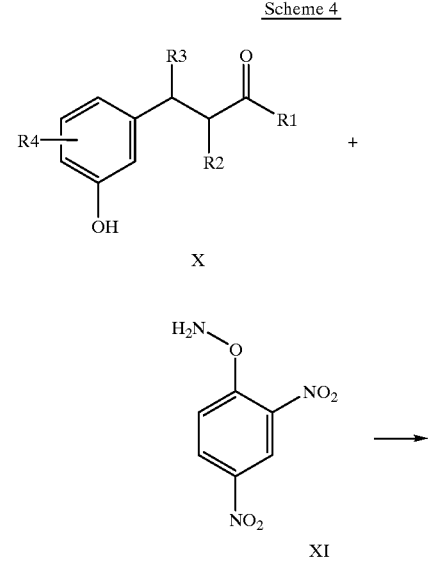

The compounds of formula XIV may also be prepared by a formylation reaction of a quinoline derivative of formula V, which is carried out by means of palladium catalysis according to the process described by H. Kotsuki et al. (Synthesis 1996: 470–472).

There are many preparations, known to those skilled in the art, for the compounds of formula V according to the invention, among which some which have been employed use the processes below.

Thus, the compounds of formula V may be prepared, according to Scheme 3, by a Skraup or a Doebner-Miller reaction. The reaction conditions used are those defined by P. Belser (Tetrahedron 1996; 52: 2937–2944) or by Z. Song (J. Heterocyclic Chem. 1993; 30: 17–21).

Scheme 3

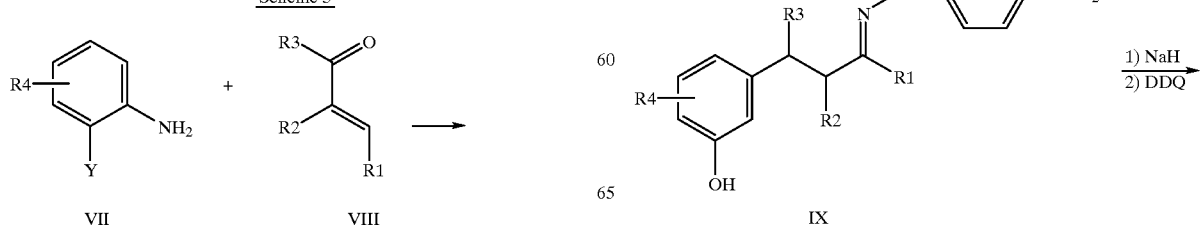

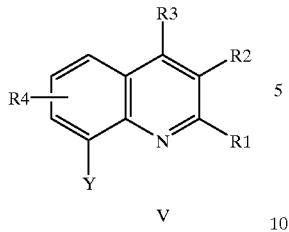

According to this process, the cyclization is obtained by treating a phenethyl ketone oxime of formula IX in the presence of sodium hydride and of an oxidizing agent such as 2,3-dichloro-5,6-dicyano-1,4-benzoquinone (DDQ). The oxime of formula IX is obtained from the condensation, which is known to those skilled in the art, between the phenyl ethyl ketone of formula X and the hydroxylamine of formula XI. The meanings of $R_1$, $R_2$, $R_3$ and $R_4$ in the compounds of formulae V, IX, X and XI are those given in formula I.

Moreover, the compounds of formula V may be prepared, according to Scheme 5, by a condensation reaction of a β-keto ester of formula XIII, in which R represents a $C_{1-4}$ alkyl group, onto an aniline of formula VII, in which Y represents an O—$CH_3$ group, by heating in a high-boiling solvent, such as diphenyl ether, to give a 4-quinolone of formula XII. This compound is then aromatized in a manner known to those skilled in the art, to give the compounds of formula V. The meanings of $R_1$, $R_2$, $R_3$ and $R_4$ in the compounds of formulae V, VII, XII and XIII are those given in formula (I).

Scheme 5

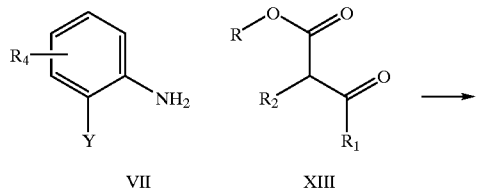

The compounds of formula V for which $R_1$ represents a methyl may be derivatized to give other compounds of formula V in which $R_1$ represents a carbonyl, a cyano, a carboxamide or a $C_{1-6}$ alkoxycarbonyl, $C_{1-6}$ hydroxyalkyl, hydroxycarbonyl or $C_{1-6}$ alkoxyalkyl group. To do this, the methyl in position 2 of the quinoline may be selectively oxidized and then derivatized. The oxidation reaction is carried out by treatment with selenium dioxide in a solvent such as dioxane (under the conditions defined by Ferranti, A. Farmaco, 1993, 48 (11), 1547–1553), to give compounds of formula V for which $R_1$ represents an aldehyde. From this aldehyde, many functionalizations, which are known to those skilled in the art, such as the addition of an organo-magnesium reagent or the oxidation to an acid and derivatization of this acid to esters, amides or nitriles, give compounds of formula V to which $R_1$ represents a cyano, a carboxamide, a hydroxycarbonyl or a $C_{1-6}$ alkoxycarbonyl, $C_{1-6}$ hydroxyalkyl or $(C_{1-6})$alkoxy$(C_{1-3})$alkyl group.

2. Alternatively, the compounds of formula (I), in which A is a $C_{1-6}$ alkoxy group and B and D together represent an oxo group according to the invention, may be prepared according to the reaction scheme (6) below:

Scheme 6

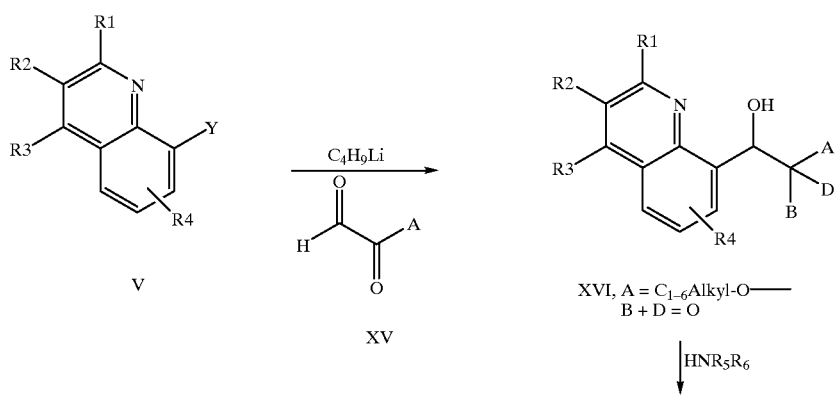

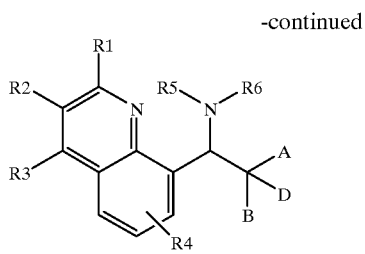

(I) A = OH, B = D = H

← Reduction

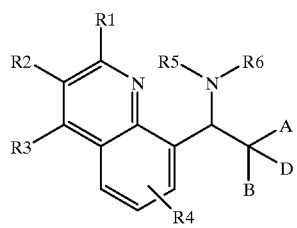

(I)

According to this process, a halo derivative of formula V, in which Y represents a halogen, is metallated as defined above, for example using butyllithium, and this product is then reacted with the alkyl glyoxylate of formula XV. The reaction may be carried out in an organic solvent such as tetrahydrofuran. The hydroxyl group in the compound of formula XVI may be activated by methods known to those skilled in the art, so as to obtain a nucleofugal group, such as a mesyl or tosyl group or a bromine atom, and it is then reacted with an amine $NHR_5R_6$, as defined above.

The compounds of formula (I), in which A is a $C_{1-6}$ alkoxy group and B and D are an oxo group according to the invention, may also be prepared by reacting an organozinc derivative of the halo derivative of formula V with a compound obtained beforehand by reacting a secondary amine of formula $HNR_5R_6$, for which the meanings $R_5$ and $R_6$ are those given for formula (I) except the hydrogen atom, with benzotriazole and the alkyl glyoxylate of formula XV or glyoxal monoacetal, according to the process described by Katrizky et al. (Synthesis 1989, 323; Synthesis 1990, 1173).

3. The compounds of formula (I), in which A is a $C_{1-6}$ alkoxy group and B and D are an oxo group, may be reduced, by conventional methods known to those skilled in the art, to give the compounds of formula (I) in which A is a hydroxyl group and B and D are hydrogen. Such methods are described, for example, in Advanced Organic Chemistry (J. March, 3rd Ed., John Wiley & Sons, Inc., New York, p. 1101). For example, the reaction may be carried out by the action of lithium aluminium hydride in an organic solvent such as tetrahydrofuran.

4. Moreover, the compounds of formula (I) according to the invention, for which A is not a hydroxyl group, may also be prepared from the compound of formula I, in which A is a hydroxyl group, by activating this group, in a manner which is known to those skilled in the art, so as to obtain a nucleofugal group W, such as a mesyl or tosyl group or a bromine atom, and from this compound by reacting it with a nucleophilic group "A", "A" representing the nucleophile corresponding to A whose meaning is given for formula (I), according to the reaction scheme (7) below:

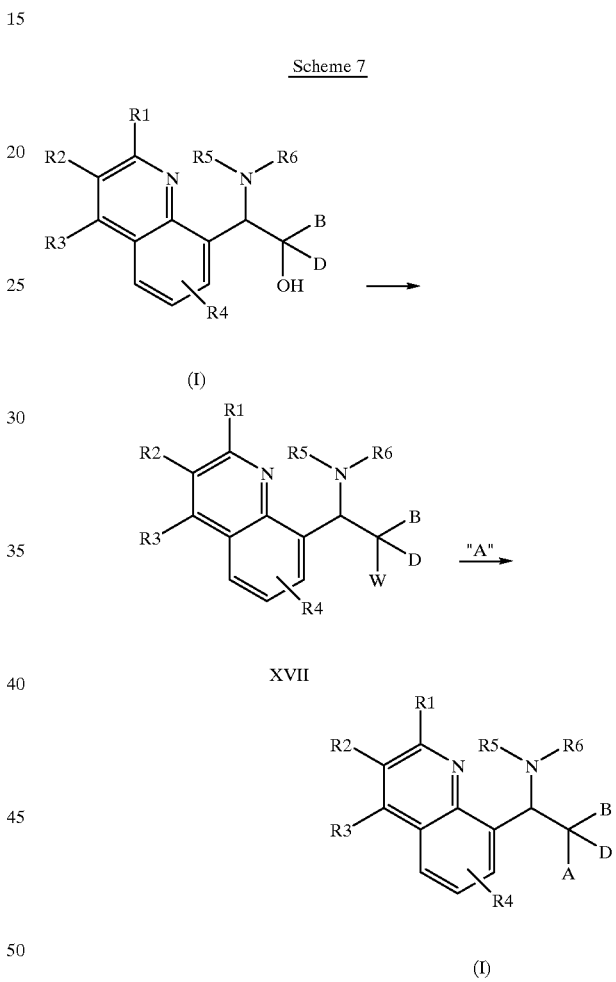

Scheme 7

5. Alternatively, the compounds of formula (I) according to the invention, for which A is a hydrogen atom, may also be prepared by dehydroxylation of a corresponding compound of formula (I), in which A is a hydroxyl group. The dehydroxylation reaction may be carried out, in a manner which is known to those skilled in the art, by reaction with triethylsilane and trifluoroacetic acid.

The compounds of formula (I) according to the invention, for which A is a hydrogen atom, may also be prepared according to the reaction scheme (8) below:

Scheme 8

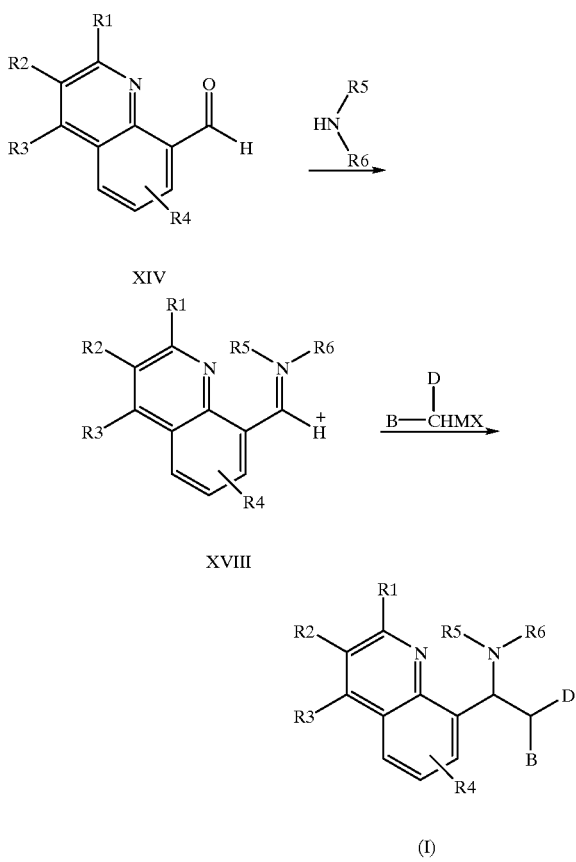

According to this process, the compound of formula (I) is prepared by reacting a nucleophilic derivative of formula B(D)—CHMX, for which M represents a metal, Y represents a halogen and B and D have the meaning given for formula (I), such as, for example, an organomagnesium or organolithium reagent, with an imine derivative of formula XVIII obtained by reacting a secondary amine of formula $NHR_5R_4$, for which the meanings of $R_4$ and $R_5$ are those given for formula (I) except for a hydrogen atom, with an aldehyde of formula XIV. The meanings of $R_1$, $R_2$, $R_3$, $R_4$, B and D are those given for formula (I).

The starting materials for the syntheses of the compounds of formula (I) are directly commercially available, are known in the literature or may be synthesized by standard methods known to those skilled in the art.

The examples which follow illustrate suitable processes and techniques for preparing this invention, without, however, limiting the scope of the claim. The microanalyses and the NMR and IR spectra confirm the structures of the compounds.

EXAMPLE 1

2,3-Dimethyl-8-(1-diethylamino-2-hydroxyethyl) quinoline pamoate (1) 2,3-Dimethyl-4-hydroxy-8-methoxyquinoline 12.3 g of 2-methoxyaniline, 14.2 g of ethyl 2-methylacetoacetate and 3 drops of 1N HCl are introduced into a 250 ml three-necked flask fitted with Dean-Stark apparatus and a condenser. The mixture is stirred overnight. 100 ml of toluene are added and the mixture is refluxed until distillation of the toluene/water azeotrope is complete. The toluene is then evaporated off and 100 ml of diphenyl ether are added. The mixture is heated at 200° C. for 1 h. 50 ml of diphenyl ether are evaporated off and the mixture is cooled to room temperature. 20 ml of petroleum ether are added and the product which crystallizes is filtered off. 2.1 g (yield: 10%) of 2,3-dimethyl-4-hydroxy-8-methoxyquinoline are obtained—m.p.: >290° C.

(2) 2,3-Dimethyl-4-chloro-8-methoxyquinoline 2.09 g of 2,3-dimethyl-4-hydroxy-8-methoxy-quinoline, 10 ml of phosphorus oxychloride and 0.43 g of phosphorus pentachloride are introduced into a 25 ml two-necked flask fitted with a condenser. The mixture is refluxed for 1 h. The reaction medium, cooled to room temperature, is poured onto 100 g of ice and extracted with ethyl acetate (2×100 ml). The organic phases are combined, washed with saturated sodium bicarbonate solution (200 ml), dried over magnesium sulphate and concentrated. The residue is purified by column chromatography on silica (elution solvent: dichloromethane). 0.85 g (yield: 37%) of 2,3-dimethyl-4-chloro-8-methoxyquinoline is obtained—m.p.: 130° C.

(3) 2,3-Dimethyl-8-methoxyquinoline 1.23 g of 2,3-dimethyl-4-chloro-8-methoxy-quinoline, 1 g of ammonium acetate, 20 ml of acetic acid and 1.2 g of palladium-on-charcoal (5%) are introduced into a Parr flask. The mixture is subjected to a hydrogen pressure of 50 psi for 4 h. The reaction medium is filtered and neutralized with 75 ml of 1 N sodium hydroxide. This mixture is extracted with ethyl acetate (2×75 ml). The organic phases are combined, dried over magnesium sulphate and concentrated. 1.32 g (yield: 77%) of 2,3-dimethyl-8-methoxyquinoline are obtained—m.p.: 138–139° C.

(4) 2,3-Dimethyl-8-hydroxyquinoline 1.25 g of 2,3-dimethyl-8-methoxyquinoline and 10 ml of 48% hydrobromic acid are introduced into a 25 ml two-necked flask fitted with a condenser. The mixture is heated at 100° C. for 24 h. The reaction mixture, cooled to room temperature, is neutralized with concentrated (30%) sodium hydroxide solution. 100 ml of water are added and the mixture is extracted with ethyl acetate (2×100 ml). The organic phases are combined, dried over magnesium sulphate and concentrated. 0.79 g (yield: quantitative) of 2,3-dimethyl-8-hydroxycuinoline is obtained—m.p.: 170° C.

(5) 2,3-Dimethyl-8-trifluoromethanesulphonatoquinoline 0.79 g of 2,3-dimethyl-8-hydroxyquinoline, 8 ml of dimethylformamide, 1.21 g of 4-nitrophenyl trifluoromethanesulphonate and 0.62 g of potassium carbonate are introduced into a 25 ml two-necked flask. The reaction medium is stirred for 2 h and is then poured into 100 ml of ethyl acetate. The organic phase is separated out after settling and is successively washed with water (50 ml) and brine (3×50 ml). The organic phases are combined, dried over magnesium sulphate and concentrated. The residue is purified by column chromatography on silica (elution solvent: 1/20 ethyl acetate/cyclohexane). 0.396 g (yield: 29%) of 2,3-dimethyl-8-trifluoromethanesulphonatoquinoline (purity: 84%) is obtained in the form of an oil.

(6) 2,3-Dimethyl-8-vinylquinoline 0.38 g of 2,3-dimethyl-8-trifluoromethane-sulphonatoquinoline, 10 ml of dioxane, 0.44 ml of tributylvinyltin, 0.19 g of lithium chloride and 0.08 g of tetrakis(triphenylphosphine)palladium are introduced into a 25 ml two-necked flask fitted with a condenser. The reaction medium is degassed by bubbling nitrogen through for 30 minutes and is then refluxed for 3 h. The solvent is evaporated off and the residue is purified by column chromatography on silica (elution solvent: 1/40 ethyl acetate/ cyclohexane). 0.169 g (yield: 68%) of 2,3-dimethyl-8-vinylquinoline is obtained in the form of an oil.

(7) 2,3-Dimethyl-8-(1,2-dihydroxyethyl)quinoline 1.17 g (10 mmol) of N-methylmorpholine N-oxide, 10 ml of water and 30 ml of acetone are placed in a 100 ml three-necked flask. 0.4 mol of a solution containing 1% by mass of osmium tetroxide in tert-butanol is added dropwise, followed by addition of a solution of 1.4 g (7.6 mmol) of 2,3-dimethyl-8-vinyl-quinoline in 10 ml of acetone. The reaction mixture is stirred for 2 hours at room temperature. 50 ml of water are added and the resulting mixture is extracted with ethyl acetate (3×100 ml). The organic phases are combined, washed with 100 ml of 1% sodium bisulphite solution and 100 ml of 1% sodium bicarbonate solution, dried over magnesium sulphate and concentrated. The residue is purified by chromatography on a column of silica (elution solvent: 30% ethyl acetate in cyclohexane). 1.34 g (yield: 81%) of 2,3-dimethyl-8-(1,2-dihydroxyethyl)quinoline are obtained in the form of a white solid. m.p. =120° C.

(8) 2,3-Dimethyl-8-(1-hydroxy-2-[tert-butyldimethyl-silyloxy]ethyl)quinoline 1.32 g (6.1 mmol) of 2,3-dimethyl-8-(1,2-dihydroxyethyl) guinoline, 0.2 ml of N,N-dimethylformamide, 50 ml of dichloromethane and 0.612 g (9 mmol) of imidazole are placed in a 100 ml round-bottomed flask. The mixture is cooled to 0° C., 1.0 g (6.6 mmol) of tert-butyldimethylchlorosilane are added and the resulting mixture is stirred for 2 hours at 0° C. 50 ml of water are added and this mixture is extracted with ethyl acetate (3×100 ml). The organic phases are combined, dried over magnesium sulphate and concentrated. The residue is purified by chromatography on a column of silica (elution solvent: 10% ethyl acetate in hexane). 1.68 g (yield: 83%) of 2,3-dimethyl-8-(2-[tert-butyldimethylsilyloxy)-1-hydroxyethyl) quinoline are obtained in the form of an oil.

(9) 2,3-Dimethyl-7-(1-diethylamino-2-[tert-butyl-dimethylsilyloxy]ethyl)quinoline 1.04 g (3.15 mmol) of 2,3-dimethyl-8-(1-hydroxy-2-[tert-butyldimethylsilyloxy]-1-hydroxy-ethyl)quinoline, 20 ml of ethyl ether and 0.53 ml (3.77 mmol) of triethylamine are introduced into a 100 ml round-bottomed flask. The mixture is cooled to −30° C. by a bath of cardice in acetone and 0.30 ml (3.9 mmol) of mesyl chloride are added. The cooling bath is removed and the reaction mixture is allowed to warm to room temperature over 30 minutes. 100 ml of water are added and the resulting mixture is extracted with ethyl ether (3×100 ml). The organic phases are combined, dried over magnesium sulphate and concentrated. The residue is transferred, without further purification, into a 25 ml three-necked flask fitted with a condenser. 6.5 ml (63 mmol) of diethylamine and 5 ml of chloroform are added and this mixture is refluxed for 16 hours. The reaction mixture is cooled to room temperature and concentrated under vacuum, 50 ml of water are added and the resulting mixture is extracted with ethyl acetate (3×50 ml). The organic phases are combined, dried over magnesium sulphate and concentrated under vacuum. The residue is purified by chromatography on a column of silica (elution solvent: 10% methanol in dichloromethane). 0.64 g (yield: 53%) of 2,3-dimethyl-8-(1-diethylamino-2-[tert-butyldimethylsilyloxy]ethyl) quinoline is obtained in the form of an oil.

(10) 2,3-Dimethyl-8-(1-diethylamino-2-hydroxyethyl)-quinoline 0.60 g (1.55 mmol) of 2,3-dimethyl-8-[1-diethylamino-2-[tert-butyldimethylsilyloxy]-ethyl]quinoline and 5 ml of tetrahydrofuran are introduced into a 50 ml round-bottomed flask. This solution is cooled to 0° C. on an ice bath and a solution of 0.60 g (2.3 mmol) of tert-butylammonium fluoride trihydrate in 10 ml of tetrahydrofuran is added. The reaction mixture is stirred at 0° C. for 1 hour and at room temperature for 16 hours. 50 ml of water are added and the resulting mixture is extracted with ethyl ether (3×50 ml). The organic phases are combined, dried over magnesium sulphate and concentrated under vacuum. The residue is purified by chromatography on a column of silica (elution solvent: 5% methanol in dichloromethane). 0.4 g (yield: 95%) of 2,3-dimethyl-8-(1-diethylamino-2-hydroxy) quinoline is obtained in the form of an oil.

(11) 2,3-Dimethyl-8-(1-diethylamino-2-hydroxyethyl)-quinoline pamoate

One equivalent of pamoic acid is added to the 2,3-dimethyl-8-[1-diethylamino-2-hydroxyethyl)quinoline and the mixture is slurried in acetone and then filtered. Water is added to the filtrate and the precipitate is filtered off and dried in a desiccator over $P_2O_5$ to give 2,3-dimethyl-8-(1-diethylamino-2-hydroxyethyl)quinoline pamoate in the form of a yellow solid—m.p.: 228° C.

EXAMPLE 2

Asymmetric synthesis of (+)-2-ethyl-3-methyl-8-(1 (R)-diethylamino-2-hydroxyethyl)quinoline hydrochloride (1) (+)-2-Ethyl-3-methyl-8-(1(S),2-dihydroxyethyl)-quinoline 2.0 g of 2-ethyl-3-methyl-8-vinylquinoline, 65 ml of t-butanol and 65 ml of water are introduced into a 250 ml round-bottomed flask. The solution is cooled to 0° C. on an ice bath and 16.8 g of AD-mix-α (complex based on $K_2OsO_2(OH)_4$, $Fe(CN)_6$ and dihydroquinidine 1,4-phthalazinediyl diether as ligand) are added. Stirring is continued for 18 h at 0° C. and a solution of 12.6 g of sodium sulphite in 30 ml of water is added. The mixture obtained is stirred for 1 h at room temperature and is then extracted with ethyl acetate (2×200 ml). The organic phase is dried over magnesium sulphate and concentrated. The residue is purified by column chromatography on silica (elution solvent: 3/7 ethyl acetate/heptane). 2.0 g (yield: 86.5%) of (+)-2-ethyl-3-methyl-8-(1(S),2-dihydroxyethyl)quinoline are obtained in the form of a white solid.

m.p.: 66° C., $[\alpha]_D^{20}$=+33.9° (C=1, methanol), enantiomeric excess: 95% by chiral HPLC.

(2): (+)-2-Ethyl-3-methyl-8-(1(S)-hydroxy-2-[tert-butyldimethylsilyloxy]ethyl)quinoline 1.72 g (7.45 mmol) of (−)-2-ethyl-3-methyl-8-(1(R),2-dihydroxyethyl)quinoline, 25 ml of dichloromethane and 0.75 g of imidazole are introduced into a 100 ml round-bottomed flask. The mixture is cooled to 0° C., 1.12 g (7.45 mmol) of tert-butyldimethylchlorosilane are added and the resulting mixture is stirred for 2 hours at 0° C. 50 ml of water are added and this mixture is extracted with ethyl acetate (3×80 ml). The organic phases are combined, dried over magnesium sulphate and concentrated. The residue is purified by chromatography on a column of silica (elution solvent: 10% ethyl acetate in hexane). 1.85 g (yield: 72%) of (+)-2-ethyl-3-methyl-8-(1(S)-hydroxy-2-[tert-butyldimethylsilyloxy]-ethyl)quinoline are obtained in the form of an oil.

(3): (+)-2-Ethyl-3-methyl-8-(1(R)-diethylamino-2-[tert-butyldimethylsilyloxy]ethyl)quinoline 1.85 g (5.35 mmol) of (+)-2-ethyl-3-methyl-8-(1(S)-hydroxy-2-[tert-butyldimethylsilyloxy]ethyl)-quinoline, 65 ml of ethyl ether and 1.33 ml (9.6 mmol) of triethylamine are introduced into a 250 ml round-bottomed flask. The mixture is cooled to −30° C. on a bath of cardice in acetone and 0.67 g (8.53 mmol) of mesyl chloride is added. The cooling bath is removed and the reaction mixture is allowed to warm to room temperature over 30 minutes. 100 ml of water are added and the resulting mixture is extracted with ethyl ether (3×50 ml). The organic phases are combined, dried over magnesium sulphate and concentrated. A portion of the residue (0.8 g of the 2.5 g obtained) is transferred, without further purification, into a 50 ml three-necked flask fitted with a condenser. 2.5 ml (34.6 mmol) of diethylamine and 3 ml of chloroform are added and this mixture is refluxed for 16 hours. The reaction mixture is cooled to room temperature and concentrated under vacuum, 50 ml of water are added and the resulting mixture is extracted with ethyl ether (3×30 ml). The organic phases are combined, dried over magnesium sulphate and concentrated under vacuum. The residue is purified by chromatography on a column of silica (elution solvent: 10% methanol in dichloromethane). 0.45 g (yield: 60%) of (+)-2-ethyl-3-methyl-8-(1(R)-diethylamino-2-[tert-butyldimethylsilyloxy]-ethyl)quinoline is obtained in the form of an oil.

(4): (+)-2-Ethyl-3-methyl-8-(1(R)-diethylamino-2-hydroxyethyl)quinoline 0.40 g (1.0 mmol) of (+)-2-ethyl-3-methyl-8-(1-diethylamino-2-[tert-butyldimethylsilyloxy]ethyl)-quinoline and 5 ml of tetrahydrofuran are introduced into a 50 ml round-bottomed flask. This solution is cooled to 0° C. on an ice bath and a solution of 0.40 g (1.52 mmol) of tert-butylammonium fluoride trihydrate in 10 ml of tetrahydrofuran is added. The reaction mixture is stirred at 45° C. for 3 hours. 50 ml of water are added and the resulting mixture is extracted with ethyl acetate (3×50 ml). The organic phases are combined, dried over magnesium sulphate and concentrated under vacuum. The residue is purified by chromatography on a column of silica (elution solvent: 5% methanol in dichloromethane). 0.25 g (yield: 87.4%) of (+)-2-ethyl-3-methyl-8-(1(R)-diethylamino-2-hydroxyethyl)quinoline is obtained in the form of an oil.

(5) (+)-2-Ethyl-3-methyl-8-(1(R)-diethylamino-2-hydroxyethyl) quinoline hydrochloride One equivalent of 0.1 N solution of hydrogen chloride in isopropanol is added to 250 mg of (+)-2-ethyl-3-methyl-8-(1(R)-diethylamino-2-hydroxyethyl)quinoline. The isopropanol is evaporated off and the product is recrystallized from acetone. 0.20 g of (+)-2-ethyl-3-methyl-8-(1(R)-diethylamino-2-hydroxyethyl)quinoline hydrochloride is obtained in the form of a white solid—m.p.: 1870° C. $[\alpha]_D^{20}=+2.01°(C=1, \text{methanol})$.

EXAMPLE 3

Using essentially the same process as that of Example 1, and using a suitable amine in step (6), other compounds of formula (I) in accordance with the invention were prepared. These compounds are given in the table below.

TABLE (I)

| No. | $R^1$ | $R^2$ | $R^3$ | $R^4$ | $R^5$ | $R^6$ | A | B(D) | salt | m.p. (° C.) | $[\alpha]_D^{20}$ |
|---|---|---|---|---|---|---|---|---|---|---|---|
| 1 | Me | Me | H | H | Et | Et | OH | H | — | oil | — |
| 2 | Me | Me | H | H | Et | Et | OH | H | pam. | 228 | — |
| 3* | Et | Me | H | H | Et | Et | OH | H | — | oil | — |
| 4* | Et | Me | H | H | Et | Et | OH | H | HCl | 187 | +2.10° (C = 1, MeOH) |
| 5* | Me | H | H | H | Et | Et | OH | H | — | oil | — |
| 6* | Me | H | H | H | Et | Et | OH | H | pam. | 128 | +13.2° (C = 1, DMSO) |
| 7* | Et | Et | H | H | Et | Et | OH | H | — | oil | — |
| 8* | Et | Et | H | H | Et | Et | OH | H | pam. | 227–229 | +11.7° (C = 1, DMSO) |
| 9* | Et | H | H | H | Et | Et | OH | H | — | oil | — |
| 10* | Et | H | H | H | Et | Et | OH | H | pam. | 228 | — |
| 11* | Me | Me | Me | H | Et | Et | OH | H | — | — | +40.1° (C = 1, DCM) |
| 12 | Me | Me | H | F | Et | Et | OH | H | — | oil | — |
| 13 | Me | Me | H | F | Et | Et | OH | H | pam. | 138–140 | — |
| 14 | H | Me | H | H | Et | Et | OH | H | — | oil | — |
| 15 | H | Me | H | H | Et | Et | OH | H | pam. | 207 | — |
| 16 | —(CH=CH)$_2$— | | H | H | Et | Et | OH | H | — | 91 | — |
| 17* | Et | Me | H | H | —CH(R)(Et)(CH$_2$)$_4$— | | OH | H | — | oil | — |
| 18* | Et | Me | H | H | —CH(R)(Et)(CH$_2$)$_4$— | | OH | H | HCl | 162 | — |
| 19* | Et | Me | H | H | —CH(S)(Et)(CH$_2$)$_4$— | | OH | H | — | oil | — |
| 20* | Et | Me | H | H | —CH(B)(Et)(CH$_2$)$_4$— | | OH | H | HCl | 175 | — |
| 21 | —(CH=CH)$_2$— | | H | H | —CH(Et)(CH$_2$)$_4$— racemic | | OH | H | — | oil | — |
| 22* | —(CH=CH)$_2$— | | H | H | —CH(Et)(CH$_2$)$_4$— racemic | | OH | H | pam. | 190–193 | +10.9° (C = 1, DMSO) |

TABLE-continued (I)

| No. | R¹ | R² | R³ | R⁴ | R⁵ | R⁶ | A | B(D) | salt | m.p. (° C.) | $[\alpha]_D^{20}$ |
|---|---|---|---|---|---|---|---|---|---|---|---|
| 23* | —(CH=CH)₂— | | H | H | Me | n-Pr | OH | H | — | | |
| 24* | —(CH=CH)₂— | | H | H | Me | n-Pr | OH | H | pam. | 236 | +5.2° (C = 1, DMSO) |
| 25* | —(CH₂)₄— | | H | H | Et | Et | OH | H | — | oil | |
| 26* | —(CH₂)₄— | | H | H | Et | Et | OH | H | HCl | 200 | |
| 27* | —(CH₂)₄— | | H | H | Me | n-Pr | OH | H | — | oil | |
| 28* | —(CH₂)₄— | | H | H | Me | n-Pr | OH | H | HCl | 90–91 | |
| 29* | H | —(CH₂)₄— | | H | Et | Et | OH | H | — | oil | — |
| 30* | H | —(CH₂)₄— | | H | Et | Et | OH | H | pam. | 179 | — |
| 31 | H | Me | H | H | Me | Et | OH | H | — | oil | |
| 32 | H | Me | H | H | Me | Et | OH | H | pam. | 205 | |
| 33* | H | Me | Me | H | Et | Et | OH | H | — | oil | |
| 34* | H | Me | Me | H | Et | Et | OH | H | HCl | 175–176 | +6.68° (C = 1, MeOH) |
| 35* | CF₃ | H | H | H | —CH(R)(Et)(CH₂)₄— | | OH | H | — | oil | |
| 36* | CF₃ | H | H | H | —CH(R)(Et)(CH₂)₄— | | OH | H | HCl | 239 | |
| 37* | Me | H | H | 6-Me | Et | Et | OH | H | — | 115–117 | +9.5° (C = 1,MeOH) |
| 38* | —(CH₂)₄— | | H | H | —CH(Et)(CH₂)₄— racemic | | OH | H | — | oil | |
| 39* | —(CH₂)₄— | | H | H | —CH(Et)(CH₂)₄— racemic | | OH | H | pam. | 199–200 | +4.9° (C = 1, MeOH) |
| 40 | Et | H | H | H | Et | Et | OH | Me (Me) | — | oil | |
| 41 | Et | H | H | H | Et | Et | OH | Me (Me) | pam. | 145–146 | |
| 42* | Et | Me | H | H | —CH(R) (Et) (CH₂)₄— | | OH | H | — | oil | |
| 43* (R) | Et | Me | H | 6-Cl | —CH(R) (Et) (CH₂)₄— | | OH | H | HCl | 191–192 | +12.7° (C = 1, MeOH) |
| 44* | Me | H | H | 7-Me | Et | Et | OH | H | — | oil | |
| 45* | Me | H | H | 7-Me | Et | Et | OH | H | HCl | 174–175 | −3.2 |
| 46* | Me | H | H | 5-Me | Et | Et | OH | H | — | oil | |
| 47* | Me | H | H | 5-Me | Et | Et | OH | H | HCl | 134–135 | +13.8 |
| 48* | Et | Me | H | H | —CH(R) (Et) (CH₂)₄— | | OH | H | — | oil | |
| 49* | Et | Me | H | H | —CH(R) (Et) (CH₂)₄— | | OH | H | HCl | 175–179 | |
| 50* | Et | Me | H | H | —CH(Me)(CH₂)3—CH(Me)— | | OH | H | — | oil | |
| 51* | Et | Me | H | H | —CH(Me)(CH₂)3—CH(Me)— | | OH | H | HCl | 209–211 | |
| 52* | Et | H | H | H | Et | Et | OH | Me | — | oil | |
| 53* | Et | H | H | H | Et | Et | OH | Me | pam. | 236 | |
| 54* | Et | H | H | H | Et | Et | OH | Me | — | oil | |
| 55* | Et | H | H | H | Et | Et | OH | Me | pam. | 226 | |
| 56* | Et | H | H | H | Et | Et | OH | Ph | — | oil | |
| 57* | Et | H | H | H | Et | Et | OH | Ph | pam. | 225 | |
| 58* | Et | H | H | H | Et | Et | OH | Ph | — | Oil | |
| 59* | Et | H | H | H | Et | Et | OH | Ph | pam. | 232–233 | |
| 60* | Et | H | H | H | Et | Et | OH | Et | — | oil | |
| 61* | Et | H | H | H | Et | Et | OH | Et | pam. | 157–164 | |
| 62* | Et | H | H | H | Et | Et | OH | Et | — | oil | |
| 63 | Et | H | H | H | Et | Et | N(OMe)Me | =O | — | oil | |
| 64 | Et | H | H | H | Et | Et | OH | =O | — | oil | |
| 65 | Et | H | H | H | Et | Et | OEt | =O | — | oil | |
| 66 | Et | H | H | H | Et | Et | Me | =O | — | oil | |
| 67 | Et | H | H | H | Et | Et | Et | =O | — | oil | |
| 68 | Et | H | H | H | Et | Et | Ph | =O | — | oil | |
| 69* | CF₃(HO)CH | Me | H | H | Et | Et | OH | H | — | 110 | |

In this table:
pam. represents a pamoic acid salt,
HCl represents a hydrochloride,
"—" represents a compound in free form,
nPr represents a linear propyl group,
cPr represents a cyclopropyl group,
i-Pr represents an isopropyl group,
Et represents an ethyl group,
Me represents a methyl group.

TABLE-continued

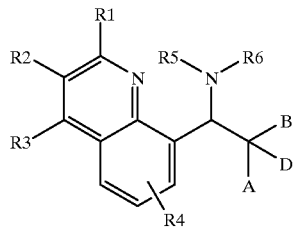

(I)

| No. | R¹ | R² | R³ | R⁴ | R⁵ | R⁶ | A | B(D) | salt | m.p. (° C.) | $[\alpha]_D^{20}$ |
|---|---|---|---|---|---|---|---|---|---|---|---|

In the B(D) column, D is indicated when it does not represent a hydrogen. Moreover, the compounds whose number is accompanied by an "*" are in chiral form for the carbon bearing the amine. (R) and (S) indicate R or S configuration of the carbon to which it is attached. All the other compounds in the table are racemic.

The compounds of the invention were subjected to biological tests intended to demonstrate their contractile activity on urethral and arterial smooth muscles.

1. The in vitro activity of the compounds of the invention was studied on urethral and arterial smooth muscles. These tests were performed on female New Zealand rabbits weighing from 3 to 3.5 kg. The animals were killed by vertebral dislocation and rings of mesenteric and urethral arterial tissue were then removed. These rings of tissue were immersed in a imodified Krebs solution and oxygenated with a mixture of 95% $O_2$ and 5% $CO_2$. Each tissue sample was subjected to a tension of 1 g and phenylephrine was then introduced at cumulative doses and the dose/response curve was established. After rinsing the samples, the test compound was introduced at cumulative doses and the dose/response curve was established. The contractile effect of each compound is evaluated by calculating the $pD_2$ (negative logarithm of the agonist concentration which induces 50% of the maximum contraction) and also by the maximum effect representing the maximum contraction percentage obtained with phenylephrine (% $E_{max}$).

The results obtained show that the compounds in accordance with the invention have:
- a urethral $pD_2$ which is usually between 4 and 8,
- an arterial $pD_2$ which is usually less than 3,
- a urethral % $E_{max}$ of greater than 30 and usually between 40 and 90,
- an arterial % $E_{max}$ which is usually less than 5.

2. The in vitro activity of the compounds of the invention were studied on saphene veins of Yucatan miniature pigs. The tissue is cut into a spiral and is mounted in an isolated organ tank in a modified Krebs solution oxygenated with a mixture of 95% $O_2$ and 5% $CO_2$ maintained at 37° C. The vessel is connected to an isometric sensor under a basal tension of 1 g and is connected to a polygraph for recording the variations in tension. The viability of each preparation is tested by prestimulation with 3 μM of noradenaline. After rinsing, the test compound is introduced and its concentration/response curve constructed cumulatively until a maximum response is obtained. The contractile effect of each compound is evaluated by calculating the $EC_{50}$ (concentration producing 50% of the maximum response).

The compounds of the invention made it possible to obtain venoconstrictive activity with an $EC_{50}$ value usually of between 1 μM and 100 μM.

The compounds of the invention may be used in the treatment of venous insufficiency and venous ulcers.

3. The in vivo activity of the compounds of the invention on urethral and blood pressure was studied in rabbits and amyelous rats, according to the following protocols:

Pithed rats

Wistar rats are anaesthetized and pithed (according to the technique described by Gillespie, MacLaren A. and Polock D., A method of stimulating different segments of the autonomic outflow from the spinal column to various organs in the pithed cat and rat; Br. J. Pharmacol., 1970, 40: 257–267).

Catheters are introduced via the femoral artery and a jugular vein. Another catheter is introduced into the urethra via an incision made in the bladder. The test compounds are administered at increasing doses via intravenous perfusion.

The results are expressed as doses (μg/kg) required to increase the urethral pressure by 10 cm of water ($UP_{10}$) or the arterial pressure by 10 mmHg ($AP_{10}$) or by 50 mmHg ($AP_{50}$).

The compounds of the invention thus tested gave:
- a $UP_{10}$ with doses of less than 500 μg/kg, usually between 5 and 200 μg/kg,
- an $AP_{10}$ with doses of greater than 600 μg/kg, usually between 600 and 2 000 μg/kg,
- an $AP_{50}$ could not be reached.

Rabbits

The experiments are carried out on female New Zealand rabbits weighing between 3 and 4 kg, anaesthetized with a mixture of ketamine and xylazine. The catheters are introduced via the descending aorta into the femoral artery, into a juglar vein and into the urethra (1.5 cm below the neck of the bladder).

The test compounds are administered 5 to 15 days following the operation, by intravenous (i.v.) administration over 5 minutes, and in a single dose (of 10 or 100 μg/kg).

In this instance, the increase in urethral pressure (UP) and in arterial pressure (AP) were measured relative to the urethral basal pressure and the arterial basal pressure, respectively. The results obtained are expressed as a percentage of premedication values at 5 minutes after intravenous (i.v.) administration.

The compounds of the invention thus tested allowed a more than 50% increase in the UP, usually between 50 and 350% after intravenous administration, and usually between 50 and 200% after force-feeding. The increase in PA was always less than 10% and is usually 0%.

The above set of results shows that the compounds of the invention have strong urethral contractile action and weak arterial contractile action.

They may be used as medicinal products, in particular as smooth muscle contracting agents, and even more particularly in the treatment of urinary stress incontinence. In this indication, the compounds according to the invention are highly effective and usually show fewer side effects than the medicinal products conventionally used for such a treatment, in particular as regards side effects affecting the cardiovascular system, in particular the arterial beds.

The compounds according to the invention may also be used for treating venous insufficiency, migraine and gastrointestinal disorders and as vasoconstrictors for the nasal mucosa.

The use of the compounds according to the invention to prepare medicinal products for treating the pathologies mentioned above forms an integral part of the invention.

According to another of its aspects, the present invention relates to pharmaceutical compositions containing a compound according to the invention as active principle.

Thus, these pharmaceutical compositions contain an effective dose of a compound according to the invention or of a pharmaceutically acceptable salt, solvate or hydrate thereof, and one or more suitable excipients.

The said excipients are chosen according to the pharmaceutical form and the desired method of administration.

In the pharmaceutical compositions of the present invention for oral, sublingual, subcutaneous, intramuscular, intravenous, topical, intratracheal, intranasal, transdermal or rectal administration, the active principles of formula (I) above or the possible salts, solvates or hydrates thereof may be administered in unit administration forms, mixed with conventional pharmaceutical vehicles, to animals and to human beings for the prophylaxis or treatment of the above disorders or diseases. The appropriate unit administration forms comprise oral forms such as tablets, gel capsules, powders, granules and oral solutions or suspensions, sublingual, buccal, intratracheal and intranasal administration forms, subcutaneous, intramuscular or intravenous administration forms and rectal administration forms. The compounds according to the invention may be used in creams, ointments or lotions for topical application.

In order to obtain the desired prophylactic or therapeutic effect, the dose of active principle may range between 1 μg and 50 mg per kg of body weight and per day. Although these doses are examples of average situations, there may be particular cases in which higher or lower doses are appropriate, and such doses also form part of the invention. According to the usual practice, the dosage which is appropriate for each patient is determined by the doctor according to the method of administration and the weight and response of the said patient.

Each unit dose may contain from 0.1 to 1 000 mg and preferably from 1 to 500 mg of active ingredients in combination with a pharmaceutical vehicle. This unit dose may be administered 1 to 5 times a day so as to administer a daily dose of from 0.5 to 5 000 mg and preferably from 1 to 2 500 mg.

For example, when a solid composition is prepared in the form of tablets, the main active ingredient is mixed with a pharmaceutical vehicle, such as gelatin, starch, lactose, magnesium stearate, talc, gum arabic or the like. The tablets may be coated with sucrose, a cellulose derivative or other materials.

According to a second example, a preparation as gel capsules is obtained by mixing the active ingredient with a diluent and pouring the mixture obtained into soft or hard gel capsules.

According to another of its aspects, the present invention also relates to a method for treating the above pathologies, which comprises the administration of a compound according to the invention.

What is claimed is:
1. A compound of formula (I)

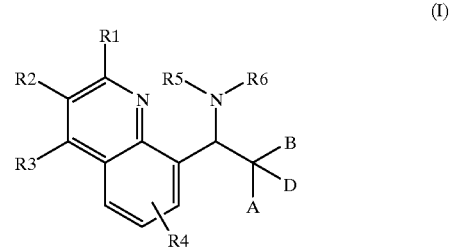

in which:
A represents a hydrogen atom, an azido, a halogen, a hydroxyl, a thiol, an amino, a phenyl, a $C_{1-6}$ akyl, $C_{1-6}$ alkylamino, di($C_{1-6}$ alkyl)amino, hydroxylamine, $C_{1-6}$ alkylhydroxylamine, $N,O-C_{1-6}$ dialkylhydroxylamine, $C_{1-6}$ alkoxy or $C_{1-6}$ alkylsulphanyl group, B and D represent, independently of each other, a hydrogen atom, a phenyl, a $C_{1-6}$ alkyl, $C_{2-6}$ alkenyl, $C_{1-6}$ fluoroalkyl or $C_{1-2}$ perfluoroalkyl group, or together form an oxo, $R_1$ represents a hydrogen atom, a halogen, a carbonyl, a hydroxycarbonyl, a cyano, a carboxamide, a $C_{1-6}$ alkyl, $C_{2-6}$ alkenyl, $C_{3-6}$ cycloalkyl, $C_{1-6}$ alkoxycarbonyl, $C_{1-6}$ hydroxyalkyl, $C_{1-6}$ alkoxy, $(C_{1-6})$alkoxy$(C_{1-3})$ alkyl, $C_{1-6}$ fluoroalkyl, $C_{1-2}$ perfluoroalkyl or $CF_3(OH)$ CH group, or $R_1$ and $R_2$ together form a $C_{3-5}$ alkylene or $C_{3-5}$ alkenylene chain or form, with the carbon atoms to which they are attached, a phenyl, $R_2$, $R_3$ and $R_4$ represent, independently of each other, a hydrogen atom, a halogen or a $C_{1-6}$ alkyl group, or $R_2$ and $R_3$ together form a $C_{3-5}$ alkylene or $C_{3-5}$ alkenylene chain or $R_1$ and $R_2$, together, are as defined above, $R_5$ and $R_6$ represent, independently of each other, a hydrogen atom, a $C_{1-6}$ alkyl, $C_{2-6}$ alkenyl, $C_{3-6}$ cycloalkyl, $C_{3-6}$ cycloalkenyl, $C_{1-6}$ fluoroalkyl or $C_{1-2}$ perfluoroalkyl group or $R_5$ and $R_6$ together form a $C_{2-6}$ alkylene or $C_{3-6}$ alkenylene chain, to give, with the nitrogen to which they are attached, a heterocycle, this heterocycle optionally being substituted with a $C_{1-4}$ alkyl group, and salts thereof, with the exception of 8-(1-aminoethyl)quinoline.

2. A compound according to claim 1 wherein:
A represents a hydroxyl, a phenyl or a $C_{1-3}$ alkyl, $N,O-C_{1-3}$ dialkylhydroxylamine or $C_{1-3}$ alkoxy group;

B and D represent, independently of each other, a hydrogen atom, a phenyl or a $C_{1-3}$ alkyl group or together form an oxo;

$R_1$ represents a $C_{1-3}$ alkyl or $C_{1-2}$ perfluoroalkyl group or $R_1$ and $R_2$ together form a $C_{3-5}$ alkylene chain, or $R_1$ and $R_2$ form, with the carbons to which they are attached, a phenyl;

$R_2$, $R_3$ and $R_4$ represent, independently of each other, a hydrogen atom, a halogen or a $C_{1-3}$ alkyl, group, or $R_2$ and $R_3$ together form a $C_3$–$C_5$ alkylene chain, or $R_1$ and $R_2$, together, are as defined above, $R_5$ and $R_6$ represent, independently of each other, a $C_{1-6}$ alkyl group, or $R_5$ and $R_6$ together form a piperidyl, this piperidyl optionally being substituted with a $C_{1-2}$ alkyl group.

3. 2,3-Dimethyl-8-(1-diethylamino-2-hydroxyethyl) quinoline, or (+)-2-ethyl-3-methyl-8-(1(R)-diethylamino-2-hydroxyethyl)quinoline according to claim 2.

4. A process for preparing a compound of formula (I) according to claim 1, in which A is a hydroxyl group wherein a compound of formula II

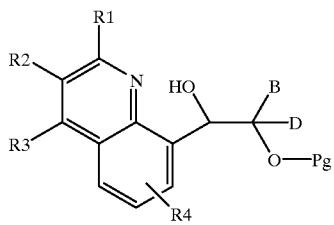

in which $R_1$, $R_3$, $R_4$, B and D are as defined in claim 1 and Pg is a protecting group, is reacted with an amine of formula $HNR_5R_6$ in which $R_5$ and $R_6$ are as defined in claim 1, followed by a deprotection.

5. A process for preparing a compound of formula (I) according to claim 1, in which A is a $C_{1-6}$ alkoxy group and B and D together are an oxo group, by reacting a compound of formula XVI

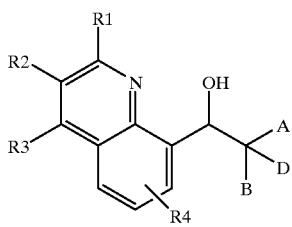

in which $R_1$, $R_2$, $R_3$ and $R_4$ are as defined in claim 1, A is a $C_{1-6}$ alkoxy group and B and D represent an oxo group, with an amine of formula $HNR_5R_6$ in which $R_5$ and $R_6$ are as defined in claim 1.

6. A process for preparing a compound of formula (I) according to claim 1, in which A is not a hydroxyl group wherein a compound of formula XVII

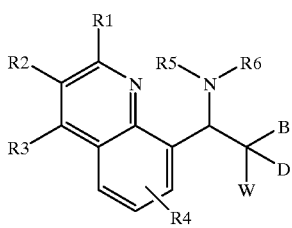

in which $R_1$, $R_2$, $R_3$, $R_4$, $R_5$, $R_6$, B and D are as defined in claim 1 and W is a nucleofugal group, is reacted with a nucleophilic group A as defined in claim 1.

7. A method of contracting smooth muscles which comprises administering to a patient in need of such treatment an effective amount of a compound of formula (I)

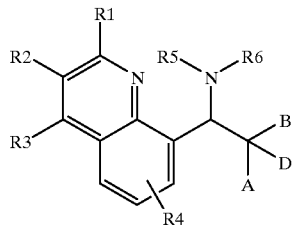

in which:
A represents a hydrogen atom, an azido, a halogen, a hydroxyl, a thiol, an amino, a phenyl, a $C_{1-6}$ alkyl, $C_{1-6}$ alkylamino, di($C_{1-6}$ alkyl)amino, hydroxylamine, $C_{1-6}$ alkylhydroxylamine, N,O—$C_{1-6}$ dialkylhydroxylamine, $C_{1-6}$ alkoxy or $C_{1-6}$ alkylsulphanyl group, B and D represent, independently of each other, a hydrogen atom, a phenyl, a $C_{1-6}$ alkyl, $C_{2-6}$ alkenyl, $C_{1-6}$ fluoroalkyl or $C_{1-2}$ perfluoroalkyl group, or together form an oxo, $R_1$ represents a hydrogen atom, a halogen, a carbonyl, a hydroxycarbonyl, a cyano, a carboxamide, a $C_{1-6}$ alkyl, $C_{2-6}$ alkenyl, $C_{3-6}$ cycloalkyl, $C_{1-6}$ alkoxycarbonyl, $C_{1-6}$ hydroxyalkyl, $C_{1-6}$ alkoxy, $(C_{1-6})$alkoxy$(C_{1-3})$ alkyl, $C_{1-6}$ fluoroalkyl, $C_{1-2}$ perfluoroalkyl or $CF_3(OH)$ CH group, or $R_1$ and $R_2$ together form a $C_{3-5}$ alkylene or $C_{3-5}$ alkenylene chain or form, with the carbon atoms to which they are attached, a phenyl, $R_2$, $R_3$ and $R_4$ represent, independently of each other, a hydrogen atom, a halogen or a $C_{1-6}$ alkyl group, or $R_2$ and $R_3$ together form a $C_{3-5}$ alkylene or $C_{3-5}$ alkenylene chain or $R_1$ and $R_2$, together, are as defined above, $R_5$ and $R_6$ represent, independently of each other, a hydrogen atom, a $C_{1-6}$ alkyl, $C_{2-6}$ alkenyl, $C_{3-6}$ cycloalkyl, $C_{3-6}$ cycloalkenyl, $C_{1-6}$ fluoroalkyl or $C_{1-2}$ perfluoroalkyl group or $R_5$ and $R_6$ together form a $C_{2-6}$ alkylene or $C_{3-6}$ alkenylene chain, to give, with the nitrogen to which they are attached, a heterocycle, this heterocycle optionally being substituted with a $C_{1-4}$ alkyl group, and salts thereof.

8. A method according to claim 7 wherein:
A represents a hydroxyl, a phenyl or a $C_{1-3}$ alkyl, N,O—$C_{1-3}$ dialkylhydroxylamine or $C_{1-3}$ alkoxy group;

B and D represent, independently of each other, a hydrogen atom, a phenyl or a $C_{1-3}$ alkyl group or together form an oxo;

$R_1$ represents a $C_{1-3}$ alkyl or $C_{1-2}$ perfluoroalkyl group or $R_1$ and $R_2$ together form a $C_{3-5}$ alkylene chain, or $R_1$ and $R_2$ form, with the carbons to which they are attached, a phenyl;

$R_2$, $R_3$ and $R_4$ represent, independently of each other, a hydrogen atom, a halogen or a $C_{1-3}$ alkyl group, or $R_2$ and $R_3$ together form a $C_3$–$C_5$ alkylene chain, or $R_1$ and $R_2$, together, are as defined, above, $R_5$ and $R_6$ represent, independently of each other, a $C_{1-6}$ alkyl group, or $R_5$ and $R_6$ together form a piperidyl, this piperidyl optionally being substituted with a $C_{1-2}$ alkyl group.

9. A method according to claim 8 wherein the compound is 2,3-Dimethyl-8-(1-diethylamino-2-hydroxyethyl) quinoline, or (+)-2-ethyl-3-methyl-8-(1(R)-diethylamino-2-hydroxyethyl)quinoline.

10. A method according to claim 7 for the treatment of urinary stress incontinence, venous insufficiency, venous ulcers, migraine or gastrointestinal disorders.

11. A method according to claim 8 for the treatment of urinary stress incontinence, venous insufficiency, venous ulcers, migraine or gastrointestinal disorders.

12. A method according to claim 9 for the treatment of urinary stress incontinence, venous insufficiency, venous ulcers, migraine or gastrointestinal disorders.

13. A method according to claim 10 for the treatment of urinary stress incontinence.

14. A method according to claim 11 for the treatment of urinary stress incontinence.

15. A method according to claim 12 for the treatment of urinary stress incontinence.

16. A pharmaceutical composition comprising a compound of the formula (I)

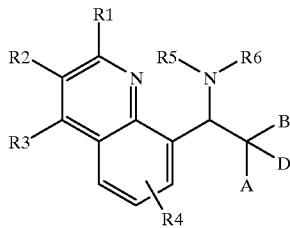

(I)

in which:

A represents a hydrogen atom, an azido, a halogen, a hydroxyl, a thiol, an amino, a phenyl, a $C_{1-6}$ alkyl, $C_{1-6}$ alkylamino, di($C_{1-6}$ alkyl)amino, hydroxylamine, $C_{1-6}$ alkylhydroxylamine, N,O—$C_{1-6}$ dialkylhydroxylamine, $C_{1-6}$ alkoxy or $C_{1-6}$ alkylsulphanyl group, B and D represent, independently of each other, a hydrogen atom, a phenyl, a $C_{1-6}$ alkyl, $C_{2-6}$ alkenyl, $C_{1-6}$ fluoroalkyl or $C_{1-2}$ perfluoroalkyl group, or together form an oxo, $R_1$ represents a hydrogen atom, a halogen, a carbonyl, a hydroxycarbonyl, a cyano, a carboxamide, a $C_{1-6}$ alkyl, $C_{2-6}$ alkenyl, $C_{3-6}$ cycloalkyl, $C_{1-6}$ alkoxycarbonyl, $C_{1-6}$ hydroxyalkyl, $C_{1-6}$ alkoxy, $(C_{1-6})$alkoxy$(C_{1-3})$ alkyl, $C_{1-6}$ fluoroalkyl, $C_{1-2}$ perfluoroalkyl or $CF_3(OH)$CH group, or $R_1$ and $R_2$ together form a $C_{3-5}$ alkylene or $C_{3-5}$ alkenylene chain or form, with the carbon atoms to which they are attached, a phenyl, $R_2$, $R_3$ and $R_4$ represent, independently of each other, a hydrogen atom, a halogen or a $C_{1-6}$ alkyl group, or $R_2$ and $R_3$ together form a $C_{3-5}$ alkylene or $C_{3-5}$ alkenylene chain or $R_1$ and $R_2$, together, are as defined above, $R_5$ and $R_6$ represent, independently of each other, a hydrogen atom, a $C_{1-6}$ alkyl, $C_{2-6}$ alkenyl, $C_{3-6}$ cycloalkyl, $C_{3-6}$ cycloalkenyl, $C_{1-6}$ fluoroalkyl or $C_{1-2}$ perfluoroalkyl group or $R_5$ and $R_6$ together form a $C_{2-6}$ alkylene or $C_{3-6}$ alkenylene chain, to give, with the nitrogen to which they are attached, a heterocycle, this heterocycle optionally being substituted with a $C_{1-4}$ alkyl group, and salts thereof, together with one or more suitable excipients.

17. A pharmaceutical composition according to claim 16 wherein:

A represents a hydroxyl, a phenyl or a $C_{1-3}$ alkyl, N,O—$C_{1-3}$ dialkylhydroxylamine or $C_{1-3}$ alkoxy group;

B and D represent, independently of each other, a hydrogen atom, a phenyl or a $C_{1-3}$ alkyl group or together form an oxo;

$R_1$ represents a $C_{1-3}$ alkyl or $C_{1-2}$ perfluoroalkyl group or $R_1$ and $R_2$ together form a $C_{3-5}$ alkylene chain, or $R_1$ and $R_2$ form, with the carbons to which they are attached, a phenyl;

$R_2$, $R_3$ and $R_4$ represent, independently of each other, a hydrogen atom, a halogen or a $C_{1-3}$ alkyl group, or $R_2$ and $R_3$ together form a $C_3$–$C_5$ alkylene chain, or $R_1$ and $R_2$, together, are as defined above, $R_5$ and $R_6$ represent, independently of each other, a $C_{1-6}$ alkyl group, or $R_5$ and $R_6$ together form a piperidyl, this piperidyl optionally being substituted with a $C_{1-2}$ alkyl group.

18. A pharmaceutical composition according to claim 17 wherein the compound is 2,3-Dimethyl-8-(1-diethylamino-2-hydroxyethyl)quinoline, or (+)-2-ethyl-3-methyl-8-(1(R)-diethylamino-2-hydroxyethyl)quinoline.

* * * * *